| United States Patent [19] | [11] | 4,057,621 |
|---|---|---|
| Pashley et al. | [45] | Nov. 8, 1977 |

[54] DESENSITIZING OXALATE DENTAL COMPOSITION AND METHOD OF TREATMENT

[76] Inventors: David H. Pashley, 427 Scotts Way, Augusta, Ga. 30904; William C. Outhwaite, Rte. 1, Box 252, N. Augusta, S.C. 29841

[21] Appl. No.: 689,110

[22] Filed: May 24, 1976

[51] Int. Cl.$^2$ .............................................. A61K 7/16
[52] U.S. Cl. .................................... 424/49; 424/317
[58] Field of Search ................................ 424/49, 317

[56] References Cited

U.S. PATENT DOCUMENTS

| 2,746,905 | 5/1956 | Baum | 424/49 |
| 3,122,483 | 2/1964 | Rosenthal | 424/49 |
| 3,689,636 | 9/1972 | Svajda | 424/49 |
| 3,863,006 | 1/1975 | Hodosh | 424/49 |

Primary Examiner—Norman A. Drezin
Attorney, Agent, or Firm—John S. Roberts, Jr.

[57] ABSTRACT

A composition and method of treatment for desensitizing hypersensitive dentin and cementum capable of effective results specially in one-treatment application. The essential ingredient or compound of the desensitizing composition is an alkali metal or ammonium oxalate where this salt may be mono- or di-substituted. The hydrogen or mono-substituted salts are preferred due to their lower pH which renders them more efficient in the protocol of this invention. These oxalates may be used effectively in the range 0.5% by weight to aqueous solution saturation. However, a range of 2.0% to solution saturation is much preferred due to the practice of the invention as a single-treatment agent. Furthermore, saturated solutions of the oxalates are most preferred also due to greater efficiency. The compositions may be used in aqueous solutions and as non-toxic paste with conventional fillers and excipients. In the paste form, the oxalate is preferred in a weight percent basis of 2-18%.

3 Claims, No Drawings

DESENSITIZING OXALATE DENTAL COMPOSITION AND METHOD OF TREATMENT

The present invention relates to a composition and method of treatment for desensitizing hypersensitive dentin and cementum capable of effective results specially in one-treatment application. In dental practice this has been found that pain from hypersensitive dentin may be exacerbated by hot and cold, sweet and sour, and by tactile contact as by brush or dental instrument. The compositions are utilized in aqueous solution or in a non-toxic dental paste. The essential ingredient or compound of the desensitizing composition is an alkali metal or ammonium oxalate and this salt may be mono- or di-substituted. The mono-substituted or hydrogen salts are preferred due to a lower pH range. The effective concentration aqueous is in the range 0.5% by weight to solution saturation. Since the effective agent, especially for a one-time application, is more effective in concentrated solutions, a preferred range in aqueous solution is from about 2.0% to solution saturation. Finally, the oxalate may be utilized as a component of a conventional non-toxic dental paste and in this modus the oxalate or salt may be utilized in the percentage of about 2–18% of the paste.

The prior art exists relative to the general background of this invention and of special interest are some literature articles of Swedish origin detailing the work of Martin Brannstrom as follows:

LITERATURE PRIOR ART

1. M. Brannstrom et al, *Caries Res.*, 1:310–317 (1967)
2. L. Linden and M. Brannstrom, *Odontologisk Revy*, 18(3):227–236 (1967)
3. M. Brannstrom and A. Astrom, *Int. Dental J.*, 22:219–227 (1972)

The articles set forth a well substantiated hypothesis which is a hydrodynamic theory of flow and displacement of the contents of the tubules under various conditions as by contact of dentin by an air jet, scraping with a proble, temperature variation, and the application of hypertonic solutions. The transmission of pain stimuli to the nerve structure located in the pulp area is mediated by a hydrodynamic link and this link consists of fluid in the tubules within the dentin. In this connection a relatively rapid movement of fluid outwardly from the pulp has been most clearly associated with pain.

PATENT PRIOR ART

U.S. Pat. No. 2,746,905 Baum — This patent is primarily directed toward the utilization of dihydroacetic acid and its water-soluble salts such as sodium, potassium, and ammonium salts and the dihydroacetic acid is utilized to maintain the pH in the mouth at a value of above 5.2 since it is stated at column 1, lines 42–45, that "inorganic tooth enamel material will be dissolved at a pH of approximately 5.2 or below." The purpose of the optional oxalate in the composition is stated at the bottom of column 1, "while the water-soluble oxalate component operates as an enamel-protective agent to increase the resistance of the tooth to acid attack." Additionally, the oxalate and the amount of oxalate component at column 2, lines 23–25, is given as a range of 0.25% to approximately 1.5% by weight. The thrust of the patent is primarily the utilization of dehydroacetic acid and neither this method nor composition is directed to a desensitizing composition for dentin; rather the composition is described at column 1, line 33, as a non-sensitizing composition.

U.S. Pat. No. 3,122,483 Rosenthal — This patent discusses the problem of hypersensitive dentin in adults who have lost some of the protective enamel sheathing on tooth surfaces and where the dentinal tubules and odontoblastic fibrils in the dentin are more surface exposed. The thrust of the patent is set out at column 2, line 22, where the patentee states that adsorption of strontium ions occurs on the odontoblastic fibrils or in the dentinal tubules, thus blocking the transmission or neural impulses from the dentinal surface to the dental pulp.

U.S. Pat. No. 3,863,006 Hodosh — In a further development, this patent utilizes potassium, lithium, or sodium nitrates either as an aqueous solution or non-toxic paste form for densensitizing hypersensitive teeth. At column 2, line 59, the patentee states that the effect of the potassium nitrate, a preferred agent, may be due either to the oxidizing nature of the compound or postulates that a crystallization takes place which blocks the dentinal tubules and protects the sensitive, nerve-filled pulp located therein.

In contrast to the above literature and patent art, the present invention utilizes an alkali metal or ammonium oxalate as the active treating agent, which, when applied to the outside of the tooth, penetrates into the tubules and fibriles of the dental dentin layer. According to the hydrodynamic theory of dentin sensitivity noted aove, painful stimuli produce shifts or movements of fluid located within the dentin tubules. The present invention is designed to reduce or eliminate fluid movement within the tubules or fibriles and thus to render the dentin incapable of transducing normally painful stimuli to the pulp in the form of fluid movement. Poiseuille's law states that fluid movement through minute tubules is proportional to the fourth power of the radius of said tubules. The present oxalate apparently reduces the functional radius of these tubules by partial or complete occlusion and this occurs where the treating solution, such as potassium oxalate $KC_2O_4H$, with a low pH (2.0) mobilizes calcium and phosphate from the hydroxyapatite crystals of hard tissues. The net result is that as soon as the ionized calcium concentration is raised so that the ion product of $[Ca^{++}] \times [\text{oxalate}]$ exceeds the solubility product constant ($K_{sp}$) of calcium oxalate, a precipitate forms on or in dentinal tubules, thereby reducing their functional radii and severely restricting fluid movement. To a lesser extent a secondary reaction occurs in that as soon as the ion product of $[\text{calcium}] \times [\text{phosphate}]$ exceeds the $K_{sp}$ of tricalcium phosphate (and other complex calcium phosphates), precipitates of these relatively insoluble salts occur within these dentinal tubules. These reactions occur rapidly and usually within one minute after applying the oxalate solution.

THE ESSENTIAL INGREDIENT

The selection of the essential salt ingredient is made from alkali metal or ammonium oxalates which may be utilized either in the mono or hydrogen form of the acid or the di-substituted salt form. Alkali metal as referred to in this specification is intended to include sodium, potassium, and lithium, these being the most prevalent and commercially interesting members of the family. It has been found that, specially for a one-application treatment by daub, the more concentrated solutions are most efficient and due to the lower acid pH of the hydrogen or mono-substituted salts, this group of compounds is preferred over the di-substituted salt. Thus, although the weight percent of the essential ingredient is operable down to about 0.5% and upwards to saturation, the preferred concentration of the essential active ingredient is from 2% aqueous solution to saturation.

Exemplary of compounds useful in the present invention, together with solubility, which is given by comparison from the 54th Edition, *Handbook of Chemistry and Physics* (1973-74), the following are listed:

| | |
|---|---|
| Dipotassium oxalate ($K_2C_2O_4 \cdot H_2O$) | 33.0 Hot Water Solubility |
| Potassium hydrogen oxalate ($KHC_2O_4$) | 16.7 Hot Water Solubility |
| Sodium oxalate ($Na_2C_2O_4$) | 6.33 Hot Water Solubility |
| Sodium hydrogen oxalate ($NaHC_2O_4 \cdot H_2O$) | 21.0 Hot Water Solubility |
| Lithium oxalate ($Li_2C_2O_4$) | 8.0 Cold Water Solubility |
| Lithium hydrogen oxalate ($LiHC_2O_4 \cdot H_2O$) | No reading |
| Ammonium oxalate [$(NH_4)_2C_2O_4 \cdot H_2O$] | 11.8 Hot Water Solubility |
| Hydrogen oxalate ($NH_4HC_2O_4 \cdot H_2O$) | No reading |

The essential or active ingredient is utilized preferably in aqueous solution and may also be utilized in paste form and with fillers and excipients common in dental preparations. Such excipients and fillers may include glycerine or a similar substance as a humidicant, a cellulose such as carboxymethyl cellulose as a filler, polyoxyethylene sorbitan monolaurate (TWEEN 20, Atlas Chemical Industries) as a surfactant, silica or similar substance as an abrasive or polishing agent, peppermint oil as a flavoring agent, and saccharin as a sweetener. In the utilization of such a paste, calcium ion is not used, since its inclusion would cause premature precipitation of the oxalate and destroy the value of the present composition as a desensitizing agent. An especially preferred active ingredient is monopotassium monohydrogen oxalate ($KHC_2O_4$).

EXAMPLE 1

A number of discs of dentin 1 mm thick with an exposed surface area of 0.317 cm² were subjected to a hydrostatic pressure of 240 cm of water. The rate of filtration through these discs was 0.85 $\mu l$ per min. (mean ± standard deviation). A solution containing 2.0% monopotassium, monohydrogen oxalate was applied to one side of the discs for 1 minute. Reapplication of the hydrostatic pressure of 240 cm of water resulted in no detectable filtration through any of these discs.

EXAMPLE 2

The same solution as was used in Example 1 was applied to a number of patients with sensitive dentin. While scraping these areas with a dental explorer was extremely painful before oxalate treatment, 1 minute after applying the oxalate solution, these areas were either much less sensitive or insensitive to scraping with an explorer. This desensitizing effect lasted months in many cases.

While any of the soluble alkali metal or ammonium oxalate salts were effective, monohydrogen monopotassium oxalate was particularly effective. It is believed that in the case of the acid salt, the acid mobilizes calcium and phosphate from the hydroxyapatite of dental hard tissue, thereby providing sufficient endogenous calcium to exceed the solubility product constant of calcium oxalate and promote its precipitation. The local elevation in phosphate concentration tends to buffer the acid as well as to cause the precipitation of complex calcium phosphates along with the calcium oxalate. The net effect was occlusion of the dentinal tubule orifice with a resultant increase in resistance to fluid flow, thereby reducing or eliminating the sensation of pain.

EXAMPLE 3

Desensitizing results in patients equivalent to Example 2 were also obtained through the application of a dentifrice or paste of the following composition:

| | Percent by Weight |
|---|---|
| Monohydrogen monopotassium oxalate | 2.0 |
| Water | 43.0 |
| Glycerin | 25.0 |
| Carboxymethyl cellulose | 2.8 |
| Polyoxyethylene sorbitan monolaurate | 2.0 |
| Micronized silica | 24.0 |
| Peppermint oil | 1.0 |
| Saccharin | 0.2 |

The above paste functioned as a desensitizing toothpaste when applied to hypersensitive teeth.

EXAMPLE 4

A water-containing toothpaste with a high concentration of oxalate was formulated as follows and utilized on patients in the same manner as Example 2 with equivalent densensitizing results:

| | Percent by Weight |
|---|---|
| Dipotassium oxalate | 18.0 |
| Water | 28.8 |
| Glycerin | 25.0 |
| Carboxymethyl cellulose | 1.0 |
| Polyoxyethylene sorbitan monolaurate | 2.0 |
| Micronized silica | 24.0 |
| Peppermint oil | 1.0 |
| Saccharin | 0.2 |

We claim:

1. A method of desensitizing hypersensitive dentin and cementum by applying to said dentin and cementum a desensitizing amount of a composition which has as the essential ingredient a member selected from the group consisting of a mono- and di-substituted alkali metal and ammonium oxalate in aqueous solution, said ingredient being applied in a desensitizing amount in a concentration of between about 2.0% by weight of said ingredient and a weight percent which is solution saturation.

2. The method of claim 1 wherein the composition is in the form of a saturated solution.

3. A method of desensitizing hypersensitive dentin and cementum by applying to said dentin and cementum a desensitizing amount of a composition which has as the essential ingredient a member selected from the group consisting of a mono- and di-substituted alkali metal and ammonium oxalate in a non-toxic dental paste form wherein said oxalate is present in between 2-18% by weight of said paste.

* * * * *